United States Patent [19]

Schrock et al.

[11] Patent Number: 5,142,073

[45] Date of Patent: Aug. 25, 1992

[54] SYNTHESIS OF MOLYBDENUM AND TUNGSTEN COMPLEXES

[75] Inventors: Richard R. Schrock, Winchester; Harold H. Fox, Boston, both of Mass.; Brian L. Goodall, Akron, Ohio

[73] Assignee: Massachusetts Institute of Technology, Cambridge, Mass.

[21] Appl. No.: 693,372

[22] Filed: Apr. 30, 1991

[51] Int. Cl.⁵ ............................................. C07F 11/00
[52] U.S. Cl. ................................................... 556/57
[58] Field of Search .......................................... 556/57

[56] References Cited

PUBLICATIONS

Schrock et al., J. Am. Chem. Soc., vol. 112, No. 10, pp. 3875–3886 (1990).
Ivin, K. J., Olefin Metathesis, Academic Press, London, 1983.
Grubbs, R. H. in Comprehensive Organometallic Chemistry, Wilkinson, G. et al., (Eds), vol. 8, Pergamon: New York (1982).
Murdzek, J. S. and R. R. Schrock, Organometallics 6: 1373 (1987).
Bazan et al., Polymer Commun. 30: 258 (1989).
Schrock, R. R. et al., in Advances in Metal Carbene Chemistry, Schubert, U. (Ed.), Kluwer Academic Publishers, Boston: 1989, p. 323.
Schrock, R. R. et al., Macromolecules 20: 1169 (1987).
Ginsburg, E. J. et al., J. Am. Chem. Soc. 111: 7621 (1989).
Swager, T. M. et al., J. Am. Chem. Soc. 111: 4413 (1989).
Edwards, D. S. et al., Organometallics 2: 1505 (1983).
Edwards, D. S., "Synthesis and Reactivity of Rhenium (VII) Neopentylidene and Neopentylidyne Complexes", MIT Doctoral Thesis (1983).
Horton, A. D. et al., Organometallics 6: 893 (1987).
Horton, A. D. and R. R. Schrock, Polyhedron 7: 1841 (1988).
Cai, S. et al., J. Am. Chem. Commun., 1489 (1988).

Primary Examiner—Jose G. Dees
Assistant Examiner—Porfirio Nazario
Attorney, Agent, or Firm—Allegretti & Witcoff

[57] ABSTRACT

Molybdenum and tungsten complexes useful as precursors for catalysts useful in the metathesis of olefins are disclosed. New compounds have the formula: $M(R_1)_2(NR_2)_2(R_3)_x$.

18 Claims, No Drawings

SYNTHESIS OF MOLYBDENUM AND TUNGSTEN COMPLEXES

BACKGROUND OF THE INVENTION

This invention relates generally to novel compounds which are useful as precursors in the preparation of catalysts which effect the metathesis of olefins, including functionalized olefins and to novel methods for their preparation. More specifically, novel compounds in accordance with embodiments of the present invention comprise transition metal based complexes which provide a facile chemical synthesis to producing corresponding transition metal based catalysts. Such complexes may be represented by the following structural formula I $$M(R_1)_2(NR_2)_2(R_3)_x \qquad (I)$$

in which M, $R_1$, $R_2$, $R_3$, and x are defined below.

In addition, the present invention also encompasses within its scope novel methods for the production of these complexes. These methods are more advantageous than prior methods because they are more economical in both the reaction time and the cost of starting materials.

The metathesis process can be defined as the redistribution of alkylidene moieties in a mixture of olefins. The simplest example is $$2R'CH=CHR \rightleftharpoons R'CH=CHR' + RCH=CHR$$

The reaction proceeds by addition of an olefin to a catalyst having a metal-carbon double bond (M=CHR, a metal-alkylidene complex) to give a metal-lacyclobutane ring, which then releases an olefin to reform a metal-alkylidene complex. A typical olefin of interest which will undergo metathesis in the presence of catalysts having a metal-carbon double bond is an ester of oleic acid, cis-CH$_3$(CH$_2$)$_7$CH=CH(CH$_2$)$_7$CO$_2$H. Three of the most active metals used in classical olefin metathesis are molybdenum, tungsten and rhenium. (Ivin, K.J., *Olefin Metathesis*, Academic Press, London, 1983; Grubbs, R.H. in *Comprehensive Organometallic Chemistry*, Wilkinson, G. et al. (Eds), Vol. 8, Pergamon New York (1982); Dragutan, V. et al., *Olefin Metathesis and Ring-Opening Polymerization of Cyolo-Olefins*, 2nd Ed., Wiley-Interscience: New York (1985); Leconte, M. et al. in *Reactions of Coordinated Ligands*, Braterman, P.R. (Ed.), Plenum: New York (1986).)

Examples of molybdenum (VI) alkylidene complexes (Murdzek, J.S. and R.R. Schrock, *Organometallics* 6: 1373 (1987); Bazan, G. et al., *Polymer Commun.* 30: 258 (1989); Schrock, R.R., Murdzek, J.S., Bazan, G.C., Robbins, J., DiMare, M., and O'Regan, M., *Synthesis of Molybdenum Imido Alkylidene Complexes and Some Reactions Involving Acyclic Olefins*, J. Am. Chem. Soc. Vol. 112, p. 3875-3886 (May 9, 1990)) and tungsten (VI) alkylidene complexes have been previously described (Schrock, R.R. et al. in *Advances in Metal Carbene Chemistry* (Schubert, U. (Ed.), Kluwer Academic Publishers, Boston: 1989, page 323; Schrock, R.R. et al., *Macromolecules* 20: 1169 (1987); Ginsburg, E.J. et al., *J. Am. Chem Soc.* 111: 7621 (1989); Swager, T.M. et al., *J. Am. Chem Soc.* 111: 4413 (1989)

Several of these compounds have been shown to catalyze the metathesis of olefins with an activity that can be controlled through the choice of the alkoxide ligand. For example, molybdenum and tungsten catalysts reported by Schrock, R.R. (U.S. Pat. Nos. 4,681,956 and 4,727,215) have been shown to homogeneously metathesize at least 250 equivalents of methyl oleate.

Several rhenium alkylidene complexes have also been reported (Edwards, D.S. et al., *Organometallics* 2: 1505 (1983); Edwards, D.S., "Synthesis and Reactivity of Rhenium (VII) Neopentylidene and Neopentylidyne Complexes", MIT Doctoral Thesis (1983); Horton, A.D. et al., *Organometallics* 6: 893 (1987); Horton, A.D. and R.R. Schrock, *Polyhedron* 7: 1841 (1988); Cai, S. et al., *J. Am. Chem.* Commun., 1489 (1988). In particular, the Edwards references describe three rhenium complexes represented by the formula Re(C-t-Bu)(CH-t-Bu)(R)$_2$ where R is a t-butoxide, trimethylsiloxide or neopentyl moiety.

The catalysts may be produced by conventional synthesis techniques as described above. A way to achieve a desirable synthesis, is to employ a precursor which itself is both economically and easily prepared. Economy in the production of a precursor is reflected in cost of its starting materials, ease of handling its starting materials, length of reaction time and number of steps required to produce the precursors.

The compounds in accordance with embodiments of the present invention comprise precursors to the synthesis of catalysts which effect the metathesis of olefins, including functionalized olefins. Therefore, a principal object of the present invention is to provide precursor compounds which may be easily synthesized using low cost materials in as few steps as possible, thus lowering the overall cost for the production of the corresponding catalyst.

BRIEF SUMMARY OF THE INVENTION

This invention relates to novel compounds useful as precursors in the preparation of catalysts and to novel methods for synthesizing such compounds. These compounds have the general formula:

$$M(R_1)_2(NR_2)_2(R_3)_x \qquad (I)$$

wherein M is molybdenum or tungsten;
N is nitrogen;
$R_1$ is halogen or triflate;
$R_2$ is phenyl or substituted phenyl, typically mono or di- $C_1$-$C_6$ alkyl substituted phenyl;
$R_3$ is Lewis base; and,
x is 0, 1 or 2.

Lewis base is herein defined as compounds which are capable of donating an electron pair. The symbols M, $R_1$, N, $R_2$, $R_3$ and x as used hereinafter in the specification and in the claims have the same meaning as defined.

In accordance with the present invention, compound I is prepared preferably in an inert, dry atmosphere by mixing molybdate or tungstate with aniline or substituted aniline, a deprotonating agent, which will deprotonate the aniline or substituted aniline, halogenating or triflating agent, a coordinating Lewis base and a suitable solvent to produce six-coordinate compounds. If a coordinating Lewis base is not employed, corresponding four-coordinate compounds are produced. While the mixture will react at room temperature, it is heated to drive the reaction to completion. The six-coordinate compounds may be recovered as solids from the reaction mixture by distillation techniques, while the corresponding four-coordinate compounds may either be retained in solution or isolated as solids.

The features and advantages of the present invention may be more clearly understood by considering the following description of preferred embodiments.

DETAILED DESCRIPTION OF PREFERRED EMBODIMENTS

The present invention relates to compounds which are represented by compound I.

Referring to I, preferred substituents are molybdenum and tungsten for M, chlorine and bromine for $R_1$, phenyl, 2,6-diisopropylphenyl, 2,6-dimethylphenyl and ortho-t-butylphenyl for $R_2$, tetrahydrofuran, 1,2-dimethoxyethane, pyridine, quinuclidine, or phosphines of the general formula, $P(R)_3$ and $(R)_2PCH_2CH_2P(R)_2$ where R is alkyl or aryl and other Lewis bases capable of donating a lone pair of electrons for $R_3$. The novel precursor compound I may be synthesized in accordance with methods of the present invention by a novel reaction as follows.

Molybdate or tungstate, for example ammonium molybdate $(NH_4)_2Mo_2O_7$, alkylammonium molybdate $[Mo_8O_{26}][CH_3N(C_8H_{17})_3]_4$ and $[Mo_8O_{26}][HN(C_{12}H_{25})_3]_4$ or their equivalent is combined under an inert atmosphere with amine of the general formula NHXAr, where Ar is phenyl or substituted phenyl, e.g. mono or di $C_1$-$C_6$ alkyl substituted phenyl, typically 1,2-diisopropylphenyl, 1,2-dimethylphenyl or ortho-tert-butylphenyl, and where X is hydrogen or trimethylsilyl as in $(CH_3)_3SiNHAr$. A compound capable of deprotonating NHXAr, for example, triethylamine, pyridine, substituted pyridine or other equivalent nitrogen bases and halogenating or triflating agent for example, $Me_3SiCl$, $Me_3SiBr$, $Me_3SiSO_3CF_3$ or their equivalent are further added to the reaction mixture. A suitable solvent is employed which may or may not contain an equivalent amount of coordinating Lewis base, for example, 1,2-dimethoxyethane (DME), tetrahydrofuran (THF), pyridine, quinuclidine, $(R)_2PCH_2CH_2P(R)_2$, and $P(R)_3$ where R =alkyl, aryl followed by heating to approximately 60°–70° C. for a minimum of 6 hours under an inert atmosphere, for example, nitrogen, yielding $Mo(NAr)_2(halogen)_2(Lewis base)_x$ where x is 0, 1 or 2.

The reaction product may be retained in solution or isolated as a solid by the evaporation of volatiles from solution using distillation techniques.

Four coordinate compounds of the present invention may be prepared, by employing non-coordinating solvents, such as toluene, diethylether, dichloromethane or trichloromethane, in the absence of coordinating Lewis bases. Compounds in accordance with embodiments of the present invention may then be used as novel precursors in the preparation of the corresponding catalysts by a three step reaction as follows.

Treatment of the compound with two equivalents of neopentyl or neophyl magnesium chloride leads to the production of an intermediate, having the general formula $M(NAr)_2(CH_2R)_2$, where M, N and Ar have been previously defined and $R = C(CH_3)_3$, $CPh(CH_3)_2$ where Ph =phenyl. Next, this complex is treated with three equivalents of a strong acid, such as triflic acid ($HOSO_2CF_3$), in 1,2-dimethoxyethane (DME), generating a six coordinate complex, $M(NAr)(CHR)(OSO_2CF_3)_2(DME)$. Two equivalents of lithium or potassium alkoxide is reacted with this complex yielding the catalyst $M(NAr)(CHR)(R')_2$ where $R'$=lithium or potassium alkoxide.

While the examples below relate to methods of preparation of novel precursor compounds containing molybdenum in accordance with embodiments of the present invention, it is to be understood that corresponding tungsten complexes can also be prepared using the methods of the present invention and employed in the same manner.

In order to further illustrate the practice of this invention, the following examples are included.

PREPARATION OF THE COMPOUNDS OF FORMULA I

EXAMPLE I

In an inert atmosphere, i.e. under a blanket of nitrogen, 10.00 grams (29.4 mmol) of ammonium molybdate,$(NH_4)_2Mo_2O_7$, were suspended in 1,2-dimethoxyethane (DME) (150 mL) at room temperature. A solution of 23.80 grams of triethylamine (235.2 mmol) in 10 mL of DME was slowly added while stirring over a period of five minutes. There was no visible change in the solution. A solution of 54.20 grams of chlorotrimethylsilane (500 mmol) in DME (20 mL) was then slowly added while stirring over a period of five minutes. The solution became white and opaque. Finally, a solution of 20.80 grams of 2,6-diisopropylaniline (118 mmol) in DME (15 mL) was added while stirring over a period of five minutes. The solution turned yellow. Additional white precipitate formed as the reaction progressed. The mixture was then heated to 70° C. for 6 hours while under an atmosphere of nitrogen. The reaction mixture was then filtered to remove the precipitate that formed during the reaction from a brick red solution. The white precipitate was washed with DME until the washings ran through colorless. The washings were combined with the brick red solution and then the volatiles were removed from solution to yield 35.12 grams (57.6 mmol, 99%) of a brick red $Mo(NAr)_2Cl_2(DME)$ product in which Ar is 2,6-diisopropylphenyl. The solid can be purified further by washing with cold pentane, if desired.

EXAMPLE II

In an inert atmosphere, i.e. under a blanket of nitrogen, 5.00 grams (14.7 mmol) of ammonium molybdate,$(NH_4)_2Mo_2O_7$, were suspended in DME (70 mL) at room temperature. A solution of 11.90 grams of triethylamine (117.6 mmol) in 10 mL of DME was slowly added while stirring over a period of 5 minutes. There was no visible change in the solution. A solution of 27.10 grams of Chlorotrimethylsilane (250 mmol) in DME (20 mL) was then added while stirring over a period of 5 minutes. The solution became white and opaque. Finally, a solution of 7.13 grams of 2,6-dimethylaniline (59 mmol) in DME (15 mL) was added while stirring over a period of 5 minutes. The solution turned yellow. Additional white precipitate formed as the reaction progressed. The mixture was then heated to 60° C. for 8 hours while under an atmosphere of nitrogen. The reaction mixture was then filtered to remove the precipitate that formed during the reaction from a brick red solution. The white precipitate was washed with DME until the washings ran through colorless. The washings were then combined with the brick red solution and then the volatiles were removed from solution to yield 14.47 grams (29.1 mmol, 98%) of the brick red Mo(NAr)₂Cl₂(DME) product in which Ar is 2,6-dimethylphenyl. The solid can be purified further by washing with cold pentane, if desired.

EXAMPLE III

The procedure of Examples I or II is repeated using an equivalent amount of alkylammonium molybdate [Mo₈O₂₆][CH₃N(C₈H₁₇)₃]₄ or [Mo₈O₂₆][HN(C₁₂H₂₅)₃]₄ to produce the Mo(NAr)₂Cl₂(DME) product in which Ar is as defined in Example I or II.

EXAMPLE IV

The procedure of Examples I, II or III is repeated using an equivalent amount of one of the following Lewis bases: tetrahydrofuran, pyridine, quinuclidine, and phosphines of the general formula P(R)₃ or (R)₂PCH₂CH₂P(R)₂ where R is alkyl or aryl to produce the corresponding product, Mo(NAr)₂Cl₂(Lewis base)ₓ where x = 1 or 2 and Ar is as defined in Examples I or II.

EXAMPLE V

The procedure of Examples I, II, III or IV is repeated using an equivalent amount of bromotrimethylsilane to produce the corresponding product, Mo(NAr)₂Br₂(Lewis base)ₓ where x = 1 or 2 and Ar is as defined in Examples I or II.

EXAMPLE VI

The procedure of Examples I, II, III or IV is repeated in the absence of a coordinating Lewis base using one of the following non-coordinating solvents to produce the corresponding four-coordinate compound Mo(NAr)₂(halogen)₂ in which Ar is as defined in Examples I or II: toluene, diethylether, dichloromethane or trichloromethane.

EXAMPLE VII

A Three Step preparation Employing Compounds of the Present Invention to Produce Corresponding Catalysts An ether solution of neopentyl magnesium chloride (98.7 mmol) was added dropwise to a stirred solution of 30.00 grams of Mo(NAr)₂Cl₂(DME) (49.3 mmol), in which Ar is as defined in Examples I or II, in 500 ml of ether at −30° C., initiating the precipitation of MgCl₂ as indicated by a color change from red to orange. The reaction mixture was allowed to warm to 25° C. and was stirred for 3 hours. The resulting mixture was filtered through Celite, and the filtrate was concentrated and kept at −40° C. yielding 20.20 grams of an orange complex.

A prechilled solution of triflic acid (35.5 mmol) in DME (20 mL) was added dropwise to a solution of 7.00 grams of the orange complex in DME (200 mL) at −30° C. over a period of 10 minutes. Some pentane (15–30 mL) may be added to aid dissolution. The solution was allowed to warm up to room temperature and stirred for 3 hours. During this period the color changed from orange to dark yellow. The solvent was then evaporated to yield a yellow solid, which was then extracted with cold toluene (100–150 mL). The extract was filtered through a bed of Celite and the toluene removed from the filtrate to give 5.9 grams (65%) of the yellow complex.

0.95 grams of solid lithium tert-butoxide (11.8 mmol) was slowly added to a solution of 4.00 grams of the yellow complex in a mixture of 200 mL ether and 20 mL DME at −30° C. over a period of 10 minutes. The reaction mixture was allowed to warm to room temperature, stirred for 2 hours, and evaporated to dryness. The dark orange catalyst was extracted with 50 mL pentane and filtered through a bed of Celite. Evaporation of the solvent gave 2.54 grams of the catalyst complex.

It is to be understood that the embodiments of the invention which have been described are merely illustrative of applications of principles of the invention. Numerous modifications may be made by those skilled in the art without departing from the true spirit and scope of the invention.

What is claimed is:

1. A compound of the general formula:

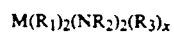

$$M(R_1)_2(NR_2)_2(R_3)_x$$

wherein M is molybdenum or tungsten; N is nitrogen; R₁ is halogen; R₂ is phenyl or substituted phenyl; R₃ is Lewis base having at least one lone pair of electrons and x is 0, 1 or 2.

2. A compound according to claim 1: wherein halogen is chlorine or bromine.

3. A compound according to claim 1: wherein said substituted phenyl is a member selected from the group consisting of 2,6-diisopropylphenyl, 2,6-dimethylphenyl, and ortho-tert butyl phenyl.

4. A compound according to claim 1: wherein said Lewis base is a member selected from the group consisting of tetrahydrofuran, 1,2-dimethoxyethane, pyridine, quinuclidine, P(R)₃ and (R)₂PCH₂CH₂P(R)₂ in which R is alkyl or aryl.

5. A compound according to claim 1: wherein M is molybdenum; N is nitrogen; halogen is chlorine; substituted phenyl is 2,6-diisopropylphenyl; and Lewis base is 1,2-dimethoxyethane.

6. A compound according to claim 1: wherein M is molybdenum; N is nitrogen; halogen is chlorine; substituted phenyl is 2,6-dimethylphenyl; and Lewis base is 1,2-dimethoxyethane.

7. A method for the production of a compound as defined in claim 1 which comprises:
   (a) mixing a molybdate or a tungstate with aniline, substituted aniline or (CH₃)₃SiNHAr in which Ar is phenyl or substituted phenyl, a deprotonating agent, a triflating or a halogenating agent, and a solvent therefor;
   (b) heating the resulting mixture to drive the reaction to completion; and
   (c) recovering the said compound I.

8. The method of claim 7 wherein said molybdate is ammonium or alkylammonium molybdate.

9. The method of claim 7 wherein said tungstate is ammonium or alkylammonium tungstate.

10. The method of claim 7 wherein said substituted aniline is a member selected from the group consisting of 2,6-diisopropylaniline, 2,6-dimethylaniline and ortho-tert-butyl aniline.

11. The method of claim 7 wherein said deprotonating agent is a member selected from the group consisting of triethylamine, pyridine and substituted pyridine.

12. The method of claim 7 wherein said halogenating agent is trimethylsilylchloride or trimethylsilylbromide.

13. The method of claim 7 wherein said triflating agent has the formula: Me₃SiSO₃CF₃.

14. The method of claim 7 wherein said solvent comprises a Lewis base.

15. The method of claim 14 wherein said Lewis base is a member selected from the group consisting of tetrahydrofuran, 1,2-dimethoxyethane, pyridine, quinuclidine, $P(R)_3$ and $(R)_2PCH_2CH_2P(R)_2$ in which R is alkyl or aryl.

16. The method of claim 7 wherein said solvent is a non-coordinating solvent.

17. The method of claim 16 wherein said solvent is a member selected from the group consisting of toluene, diethylether, dichloromethane and trichloromethane.

18. The method of claim 7 wherein the mixture is heated between 60 and 70 degrees Centigrade for at least six hours.

* * * * *